(12) United States Patent
Angel et al.

(10) Patent No.: US 6,846,674 B2
(45) Date of Patent: Jan. 25, 2005

(54) GENETICALLY MODIFIED FIBROBLAST CELLS

(75) Inventors: Peter Angel, Leimeu (DE); Norbert Fusenig, Heidelberg (DE); Andrea Kolbus, Rastatt (DE); Marina Schorpp-Kistner, Durmersheim (DE); Axel Szabowski, Heldelberg (DE); Nicole Maas-Szabowski, Heidelberg (DE); Sven Andrecht, Darmstadt (DE)

(73) Assignee: Deutsche Krebsforschungszentrum Stiftung des Offentlichen rechts, Heidelberg (DE)

( * ) Notice: Subject to any disclaimer, the term of this patent is extended or adjusted under 35 U.S.C. 154(b) by 0 days.

(21) Appl. No.: 10/196,000

(22) Filed: Jul. 15, 2002

(65) Prior Publication Data

US 2003/0109474 A1 Jun. 12, 2003

Related U.S. Application Data

(63) Continuation of application No. PCT/DE01/00131, filed on Jan. 12, 2001.

(30) Foreign Application Priority Data

Jan. 14, 2000 (DE) .......................................... 100 11 926

(51) Int. Cl.⁷ ............................ C12N 5/06; C12N 5/08; C12N 5/10
(52) U.S. Cl. ...................... 435/325; 435/325; 435/357; 435/366
(58) Field of Search ............................... 435/325, 352, 435/366, 357

(56) References Cited

FOREIGN PATENT DOCUMENTS

EP        1 055 366 A1      11/2000

OTHER PUBLICATIONS

Johnson et al, Molecular and Cellular Biology, Aug., 1996, vol. 16, No. 8, pp. 4504–4511.*

Chomczynski, Piotr, et al., "Single–Step Method of RNA Isolation by Acid Guanidinium Thiocyanate–Phenol–Chloroform Extraction", *Analytical Biochemistry, 162*, (1987), 156–159.

Riabowol, Karl, et al., "Transcription Factor AP–1 Activity is Required for Initiation of DNA Synthesis and is Lost During Cellular Aging", PNAS, vol. 89, (1992), 157–161.

Sambrook, J., et al., "5. Enzymes Used in Molecular Cloning", *Molecular Cloning. A Laboratory Manual*, (1989), 5.1–5.95.

Sambrook, J., et al., "6. Gel Electrophoresis of DNA", *Molecular Cloning. A Laboratory Manual*, (1989),6.1–6.2.

Sambrook, J., et al., "9. Analysis and Cloning of Eukaryotic Genomic DNA", *Molecular Cloning. A Laboratory Manual*, (1989),9.1–9.62.

Sambrook, J., et al., "Plasmid Vectors—Development of Plasmid Cloning Vectors", *Molecular Cloning. A Laboratory Manual*, (1989),1.7–1.10

Todaro, George J., et al., "Quantitative Studies of the Growth of Mouse Embryo Cells in Culture and Their Development into Established Lines", *The Journal of Cell Biology, 17*, (1963),299–313.

Turner, David M., "Natural Product Source Material Use in the Pharmaceutical Industry: the Glaxo Experience", *Journal of Ethnopharmacology, 51*, (1996),39–44.

Bossy–Wetzel, Ella.,et al. ,"Induction of apoptosis by the transcription factor c–Jun", *EMBO (European Molecular Biology Organization) Journal*, vol. 16, No. 7, ISSN 0261–4189 XP002174993,(1997),1695–1709.

Hans–Jurgen, Stark.,et al. ,"Organotypic Keratinocyte Cocultures in Defined Medium with Regular Epidermal Morphogenesis and Differentiation", *Journal of Investigative Dermatology*, vol. 112, No. 5 XP–002174997,(May 1999), 681–691.

Kovary, Karla.,et al. ,"The Jun and Fos Protein Families Are Both Required for Cell Cycle Progression in Firoblasts", *Molecular and Cellular Biology*, vol. 11, No. 9,(Sep. 1991), 4466–4472.

Maas–Szabowski, Nicole.,et al. ,"Organotypic Cocultures with Genetically Modified Mouse Fibroblasts as a Tool to Dissect Molecular Mechanisms Regulating Keratinocyte Growth and Differentiation", *Journal of Investigative Dermatology*, vol. 116, No. 5 XP–002174999,(May 2001), 816–820.

Orlandini, Maurizio,et al. ,"Identification of a c–fos–induced gene that is related to the platelet–derived growth factor/vascular endothelial growth factor family", *Proceedings of the National Academy of Sciences of the United States*, vol. 93, No. 21 XP–002174995,(Oct. 1996),11675–11680.

(List continued on next page.)

*Primary Examiner*—Terry McKelvey
(74) *Attorney, Agent, or Firm*—Schwegman, Lundberg, Woessner & Kluth, P.A.

(57) ABSTRACT

The invention relates to genetically modified fibroblast cells which comprise the following properties: (a) a gene, encoding a subunit of the transcription factor AP-1, of its genome is inactivated and/or a component, acting on the AP-1 transcription factor of the signal transduction pathway is modified resulting in a modified AP-1 activity; (b) functionally linked with a promoter, it contains in an expression vector the gene from (a) in a form such that the active subunit is only expressed after induction of the promoter or the subunit encoded by the gene is present in inactive form and a form that can be activated. Furthermore, the invention relates to a method which uses the fibroblast cell according to the invention to identify a compound which can support, inhibit or modify the AP-1-dependent differentiation and/or proliferation of keratinocytes or a gene which is involved in the AP-1-dependent differentiation and/or proliferation of keratinocytes as well as to the use of the test compound identified according to the method of the invention and the gene for treating or diagnosing diseases associated with a disturbed proliferation and/or differentiation of keratinocytes.

14 Claims, 8 Drawing Sheets

OTHER PUBLICATIONS

Figure 1A:
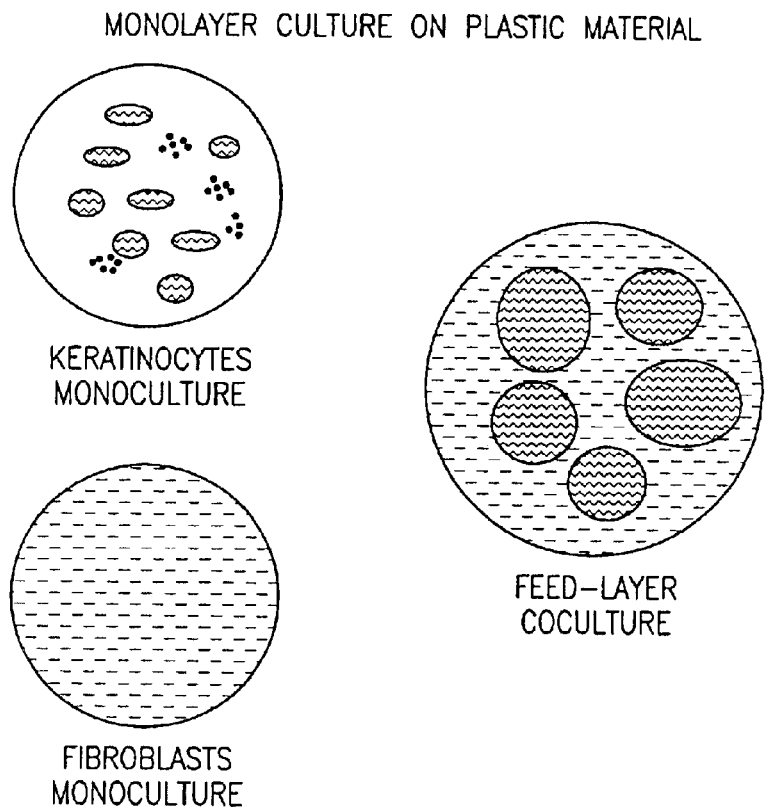

Schorpp–Kistner, Marina., et al. ,"JunB is essential for mammalian placentation", *EMBO Journal; Oxford University Press, Surrey, GB*, vol. 18, No. 4 XP–002121786,(Feb. 15, 1999),934–948.

Schreiber, Martin.,et al. ,"Control of cell cycle progression by c–June is p53 dependent", *Genes & Development*, vol. 13, No. 5 XP002174994,(Mar. 1, 1999),607–619.

Superti–Furga, Giulio.,et al. ,"Hormone–dependent transcriptional regulation and cellular transformation by Fos–steroid receptor fusion proteins", *Proceedings of the National Academy of Sciences of the United States*, vol. 88, No. 12 XP–002174996,(1991),5114–5118.

Szabowski, Axel.,et al. ,"c–Jun and JunB Antogonistically Control Cytokine–Regulated Mesenchymal–Epidermal Interaction in Skin", *CELL*, vol. 103, No. 5 XP002174998, (Nov. 22, 2000),745–755.

* cited by examiner

MONOLAYER CULTURE ON PLASTIC MATERIAL

ORGANTOYPICAL CULTURE WITH COLLAGEN GEL

GENETICALLY MODIFIED FIBROBLAST CELLS

RELATED APPLICATIONS

This application is a continuation under 35 U.S.C. 111(a) from International Application No. PCT/DE01/00131 filed Jan. 12, 2001 and published in German as WO 01/511619 A3 on Jul. 19, 2001, which claimed priority from German Application No. 100 11 926.3 filed Jan. 14, 2000, which applications and publication are incorporated herein by reference The present invention relates to genetically modified fibroblast cells in which a gene, coding for a subunit of the AP-1 transcription factor, of the genome thereof is inactivated and/or a component, acting on the AP-1 transcription factor, of the signal transduction path is modified resulting in a modified AP-1 activity and which functionally linked with the promoter contain the above-mentioned gene in an expression vector in a form such that the active subunit is only expressed after induction of the promoter or in a form such that the subunit encoded by the gene is present in inactive form which can, however, be activated. The present invention also relates to a method of identifying compounds which can support, inhibit or modify the AP-1-dependent differentiation and/or proliferation of keratinocytes and enable the identification of genes involved in the AP-1-dependent differentiation and/or proliferation of keratinocytes.

The proliferation and differentiation of keratinocytes and thus the structure and function of the epidermis are dependent on the interaction with fibroblasts, these processes at least in part depending on the controlled expression of genes which are dependent on the AP-1 transcription factor (e.g. c-Jun, JunB). It may be assumed that abnormal or lacking regulation of these genes results in a disturbed proliferation and/or differentiation of the keratinocytes, which in turn may lead to a number of diseases, e.g. a disturbed metabolism of the skin (disturbed wound healing, psoriasis, chronic inflammatory reactions, etc.) or the formation of tumors of the skin. The involved genes and/or factors are hardly known thus far and the former search for such factors, which is substantially based on pharmacological studies made in connection with cell cultures or animals and partially also on clinical studies, has the drawback that the analyses to be carried out are very complex and time-consuming and above all not very selective either.

It is thus the object of the present invention to provide products for identifying compounds directly or indirectly correlated with an expression of the AP-1 transcription factor and/or directly or indirectly regulated by this transcription factor and involved in the proliferation and/or differentiation of keratinocytes of the skin. On the one hand, these are compounds which directly control genes via the AP-1 transcription factor, are responsible for growth regulation and epidermis differentiation and are defective or regulated imperfectly in pathological states. These compounds comprise a large number of known signal substances which are not yet sufficiently known, such as interleukins and other cytokines and growth factors as well as synthetic agonists and/or antagonists for their receptors. The genes controlled by them via AP-1 and/or their products comprise a similarly large number of known still insufficiently known growth and differentiation factors, enzymes, their inhibitors and structural proteins of the epidermal cells. In addition to these components directly controlling AP-1 or dependent thereon, the test system is to detect regulating factors or proteins which are released indirectly by pathological or therapeutic influences in keratinocytes and then induce reaction mechanisms secondarily controlled by AP-1 within the genetically modified fibroblasts.

This object is achieved by providing the embodiments characterized in the claims.

It was found surprisingly in the present invention that by means of genetically modified fibroblast cells a system for identifying the above substances can be established. These fibroblast cells have the following properties: (a) a gene coding for a subunit of the AP-1 transcription factor, of its geneome is inactivated and/or a component, acting on the AP-1 transcription factor, of the signal transduction pathways is modified resulting in a modified AP-1 activity and (b) functionally linked with a promoter they contain the gene from (a) in an expression vector in a form such that the active subunit is only expressed after induction of the promoter or in a form such that the subunit encoded by the gene is present in inactive form which can, however, be activated. This genetically modified fibroblast cell line enables a more specific and simpler search for new active substances, e.g. new agonistic or antagonistic pharmacons, or for corresponding genes which can be of use for treating diseases associated with the proliferation and/or differentiation of keratinocytes. In addition, substances already identified in other systems can also be analyzed more specifically in test systems based on the fibroblast according to the invention.

An embodiment of the present invention thus relates to a genetically modified fibroblast cell having the following properties: (a) a gene coding for a subunit of the AP-1 transcription factor, of the genome thereof is inactivated and/or a component, acting on the AP-1 transcription factor, of the signal transduction pathway is modified, resulting in a modified AP-1 activity; and (b) functionally linked with the promoter it contains the gene from (a) in an expression vector in a form such that the active subunit is only expressed after induction of the promoter or in a form such that the subunit encoded by the gene is present in inactive form which can, however, be activated.

Examples of genes coding for subunits of the AP-1 transcription factor are jun-c, JunB, JunD, c-Fos, FosB, Fra-1 and members of the ATF-protein family (Angel and Karin, 1991).

The gene coding for a subunit of the AP-1 transcription factor can be inactivated according to methods known to a person skilled in the art. Here, the use of the antisense technique (Riabowol et al., 1992, PNAS 89, pp. 157–161) or the injection of neutralizing antibodies (Kovary et al., 1991, Mol. Cell. Biol. 11, pp. 4466–4472) has to be mentioned by way of example. The preferred approach of inactivating a gene is, however, the production of "knockout" (mammalian) animals and the isolation of cells derived therefrom. This comprises the production of a suitable gene-targeting vector, the isolation or correctly genetically modified embryonic non-human stem cells, the provision of (mammalian) animal blastocysts (preferably: murine blastocysts) with these cells by way of injection, the establishment of chimeras and the pairing of these (mammalian) animals to generate (mammalian) animals (preferably: mice) having the desired genotype (A. L. Joyner: Gene targeting: A practical approach, Oxford University Press, Oxford, 1993, p. 1–234). Thereafter, mammals are paired with a suitable genotype, the embryos are isolated during pregnancy (see Example 1), primary embryonic fibroblasts are isolated therefrom according to standard protocols and immortal lines are spontaneously established therefrom (Todaro and Green, 1995; Schreiber et al., 1995). Thus, a preferred embodiment of the fibroblast cell according to the invention is a fibroblast cell in which the gene coding for a subunit of the AP-1 transcription factor was inactivated by means of "knockout". The gene coding for a subunit of the AP-1 transcription factor can also be inactivated by interfering with (e.g. inhibiting) AP-1 higher regulatory proteins. In place of or in addition to the inactivation of the gene coding for a subunit of the AP-1 transcription factor the activity of AP-1 can also be modified so as to modify a component, acting on AP-1, of the signal transduction pathway. This modification can be a modification of the influencing component on the gene or protein level, e.g. an upward-regulated or downward-regulated expression or a conformational or structural change. The component thus no longer adopts its role in the signal transduction pathway as usual and effects a change in the activity of AP-1.

It is preferred to have the genes to be expressed in a suitable expression vector controlled by a constitutive promoter. Regulatory units of viruses (SV40, RSV, CMV) or of cellular genes expressed constitutively (e.g. the ubiquitin C protein) are suited for this purpose. It is preferred to design the expression vector such that a subunit of the AP-1 transcription factor is expressed constitutively in inactive form which can, however, be activated. Here, an inactive fusion protein is produced which only changes its conformation after addition of an inductor such that the protein becomes active.

In order to produce the expression vector of step (b), the person skilled in the art can use common in vitro recombination methods, as described e.g. in Sambrook et al., 1989.

In a preferred embodiment, the genetically modified fibroblast cell according to the invention is characterized in that the gene which codes for a subunit of the AP-1 transcription factor is c-jun (Angel et al., 1988; Hilberg et al., 1993), or junB (Schorpp-Kistner et al., 1999), i.e. the fibroblast cells are c-jun-deficient or JunB-deficient.

In a particularly preferred embodiment, the genetically modified fibroblast cell according to the invention is a human fibroblast cell or murine fibroblast cell, and a genetically modified fibroblast cell which contains c-JunER™ or JunB-ER™ is most preferred. c-JunER™ contains the N-terminal half of c-Jun and the tamoxifen-binding site (ER) (Bossy-Wetzel et al., 1997). In order to optimize the expression, the c-Jun-ER™ sequences are controlled by the human ubiquitin-C promoter/enhancer sequence which represents an efficient regulatory unit (Schorpp et al., 1996). On the basis of JunB a JunB-ER™ construct is prepared analogously (see Example 9).

Another embodiment of the present invention relates to a method of identifying a compound which can support, inhibit or modify the AP-1-dependent differentiation and/or proliferation of keratinocytes, the method comprising the steps of: A) contacting the test compound with the genetically modified fibroblast cell according to the invention in coculture with primary keratinocytes in a test system I and/or test system II, test system I being characterized in that the protein encoded by the gene from (b) is not available or only available in inactive form, and test system II being characterized in that the protein encoded by the gene from (b) is present in active form, and B) determining the expression of marker genes associated for the differentiation state or proliferation state of keratinocytes and/or the epithelial structures, a change in the expression of the marker genes and/or the epithelial structure in test system II only indicating incompletely in test system I that the test compound can support, inhibit or modify the AP-1-dependent differentiation and/or proliferation of keratinocytes. Although proliferation but not differentiation of the keratinocytes can be measured in test system I, test system I distinguishes itself in that keratinocytes and fibroblasts are cocultured in a two-dimensional system on (plastic) culture carriers, whereas in test system II both cell types together with a matrix form a three-dimensional tissue structure, similar to the skin.

Test system I represents a two-dimensional feeder-layer coculture in which keratinocytes together with irradiated fibroblasts (feeder cells) are cultured in submersed fashion (Rheinland and Green, 1975). Primary human keratinocytes are isolated from skin biopsies of plastic surgery, expanded in feeder layer coculture (passage 1) and introduced into the experiments in passage 2. Both irradiated, post-mitotic murine 3T3 fibroblasts and human fibroblasts or fibroblast lines can be used as a feeder layer, and the differentiation process of the epithelial cells remains unchanged, i.e. the specific markers are expressed adequately. The proliferation of the keratinocytes is induced significantly by the mesenchymal cells together with which they are cultured. Here, it is a close vicinity of epithelial and mesenchymal cells that is decisive but not the direct cell contact. This indicates a paracrine effect of the mediators produced by the mesenchymal cells (Smola et al., 1993). For example, mediators produced by keratinocytes, such as IL-1, can stimulate the feeder cells to synthesize keratinocte-specific growth factors, such as KGF (Maas-Szabowski et al., 1999), which refers to a regulatory circuit between fibroblasts and keratinocytes. Both cell types can be cocultured according to known methods, e.g. by means of the methods described in the below examples, preferably by means of the organotypical culture described in below Examples 3 and 11 to 13. However, if keratinocytes are cultured under conventional conditions in the feeder-layer system while submersed in medium, they will proliferate and, as soon as they have reached confluence, will start growing in several layers. Depending on the culturing conditions, they form one or more cell layers resembling squamous epithelia but differing considerably in vivo from the epidermis as regards structure and function.

In test system II, i.e. the much more complex, three-dimensional organotypical culture, the keratinocytes are cultured on a collagen gel admixed with fibroblasts while exposed to air (type I collagen, from rat or cow) so as to achieve an improved epithelial tissue architecture more easily comparable with the structure of the skin (Fusenig et al., 1994). Medium components diffusing through the collagen gel immersed in the medium feed the fibroblasts and keratinocytes. In organotypical cultures, the keratinocytes already form a multi-layered, orderly epithelium after only 7 days, consisting of basal layer, spinous layer, regeneratirve layer horny layer. From a morphological point of view, the epithelium corresponds to the epidermis, since it has the specific epidermal differentiation markers, such as keratin 1/10, transglutaminase, filaggrin, loricrin (Stark et al., 1999).

The test compounds may be widely differing compounds, both naturally occurring compounds and synthetic, organic and inorganic ones as well as polymers (e.g. oligopeptides, polypeptides, oligonucleotides and polynucleotides) as well as small molecules, antibodies, sugar, fatty acids, nucleotides and nucleotide analogs, analogs of naturally occurring structures (e.g. peptide imitators, nucleic acid analogs, etc.) and a number of further compounds as well as mixtures of different compounds. One the one hand, cytokines and growth factors and, on the other hand, low-molecular lipophilic substances imitating cytokine or growth factors (agonists) or inhibiting cytokine-induced or growth factor-induced signal paths (antagonists) are of special interest. Furthermore, testing of proteins is of interest, whose expression is regulated by c-Jun or JunB, e.g. the matrix metalloproteinases MMP-9 and MMP-13 (Schorpp-Kistner, 1999). Uptake into the cells is effected in the test compounds within short distances in the culture system. The direct passage of lipophilic substances takes place through the cell membrane. In the case of cytokines and growth factors, binding to corresponding surface receptors and triggering of intracellular signal paths to the cell nucleus take place. In addition, a large number of possibly useful compounds can be screened in extracts of natural products as a starting material. Such extracts may be derived from a large number of sources, e.g. the following species: fungi, actinomycetes, algae, insects, protozoa, plants and bacteria. The extracts showing activity can then be analyzed to isolate the active molecule; see in this connection e.g. Turner, 1996, and Suh, 1995.

Figure 4:
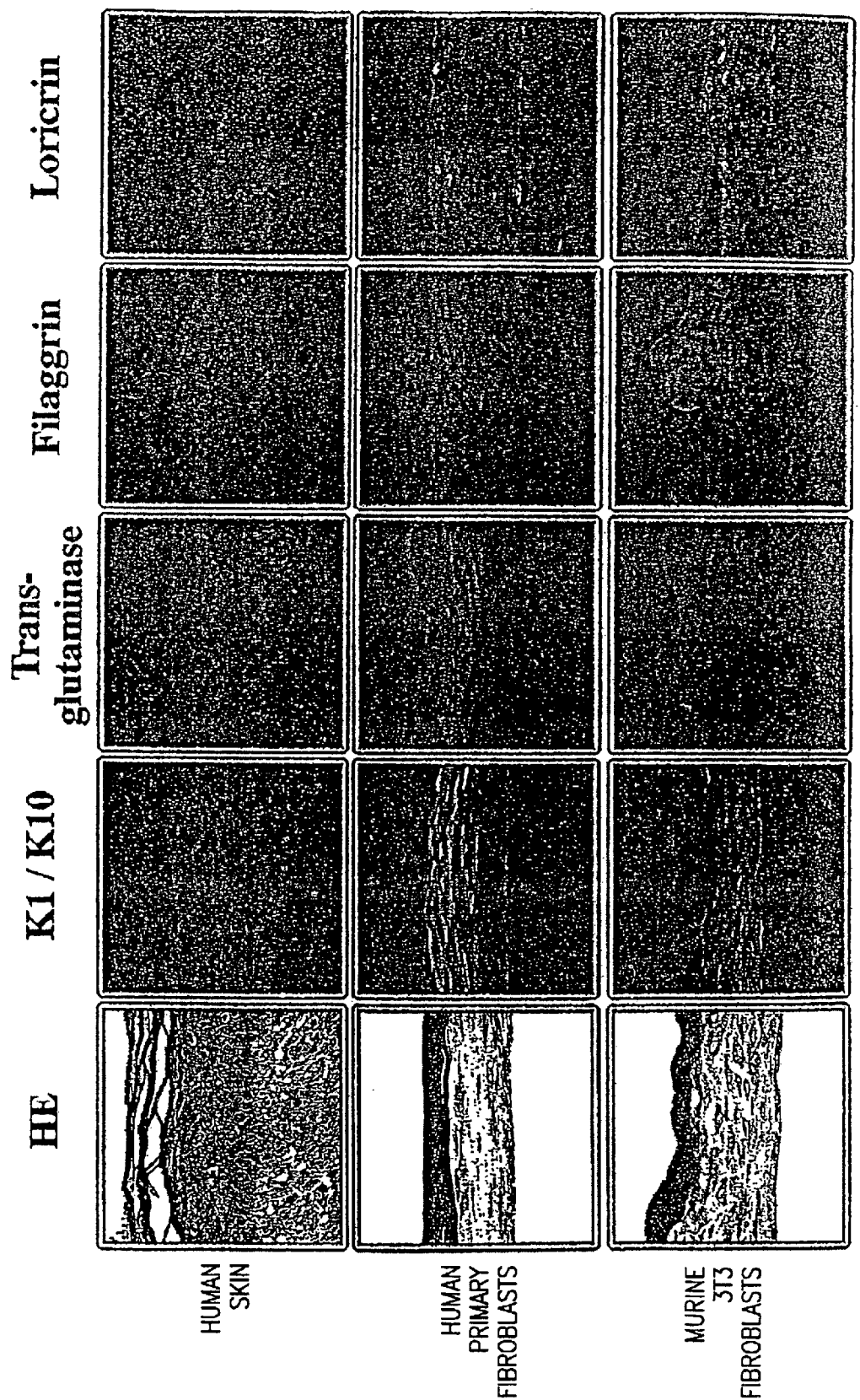
Figure 5:
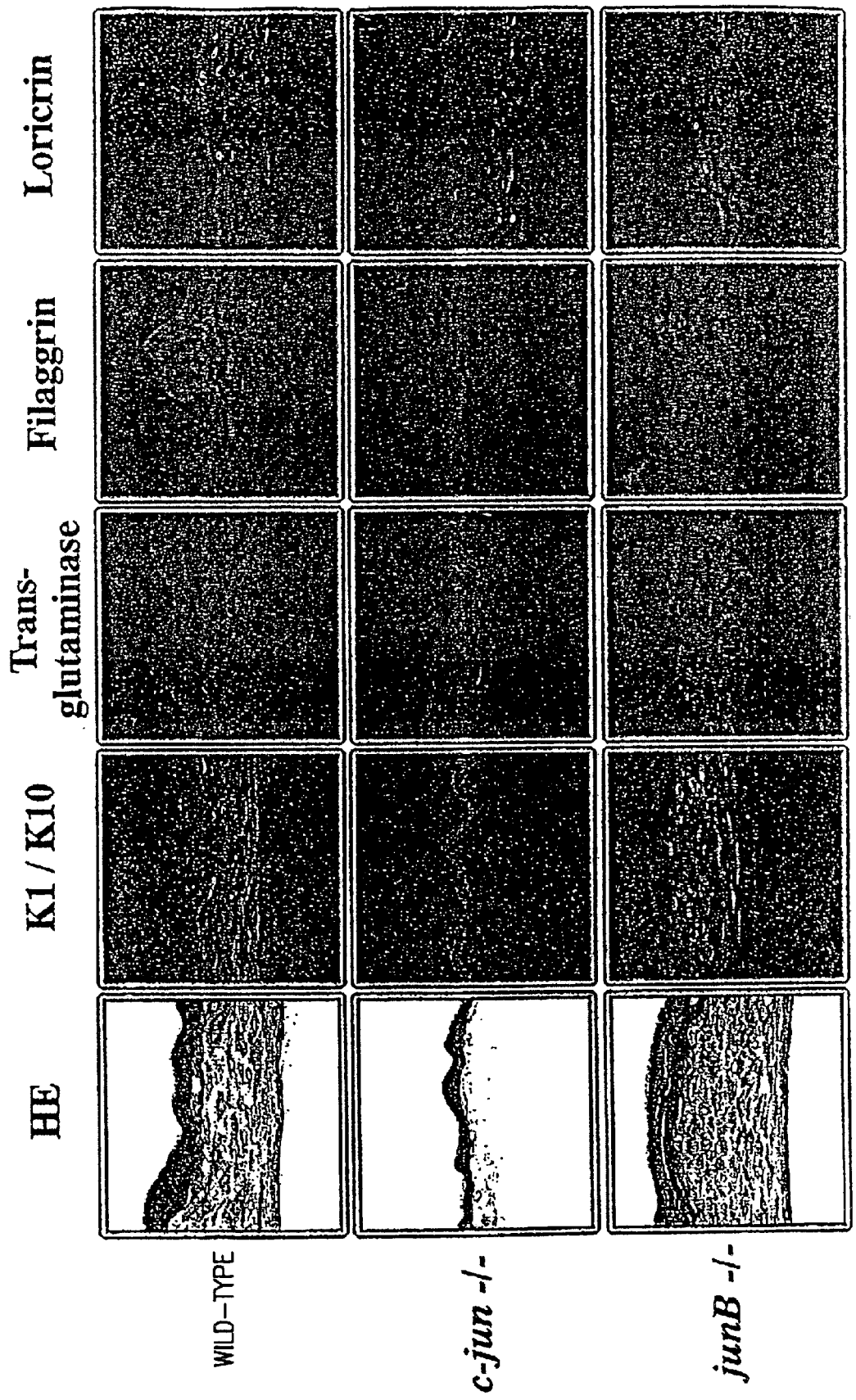
Figure 6A:
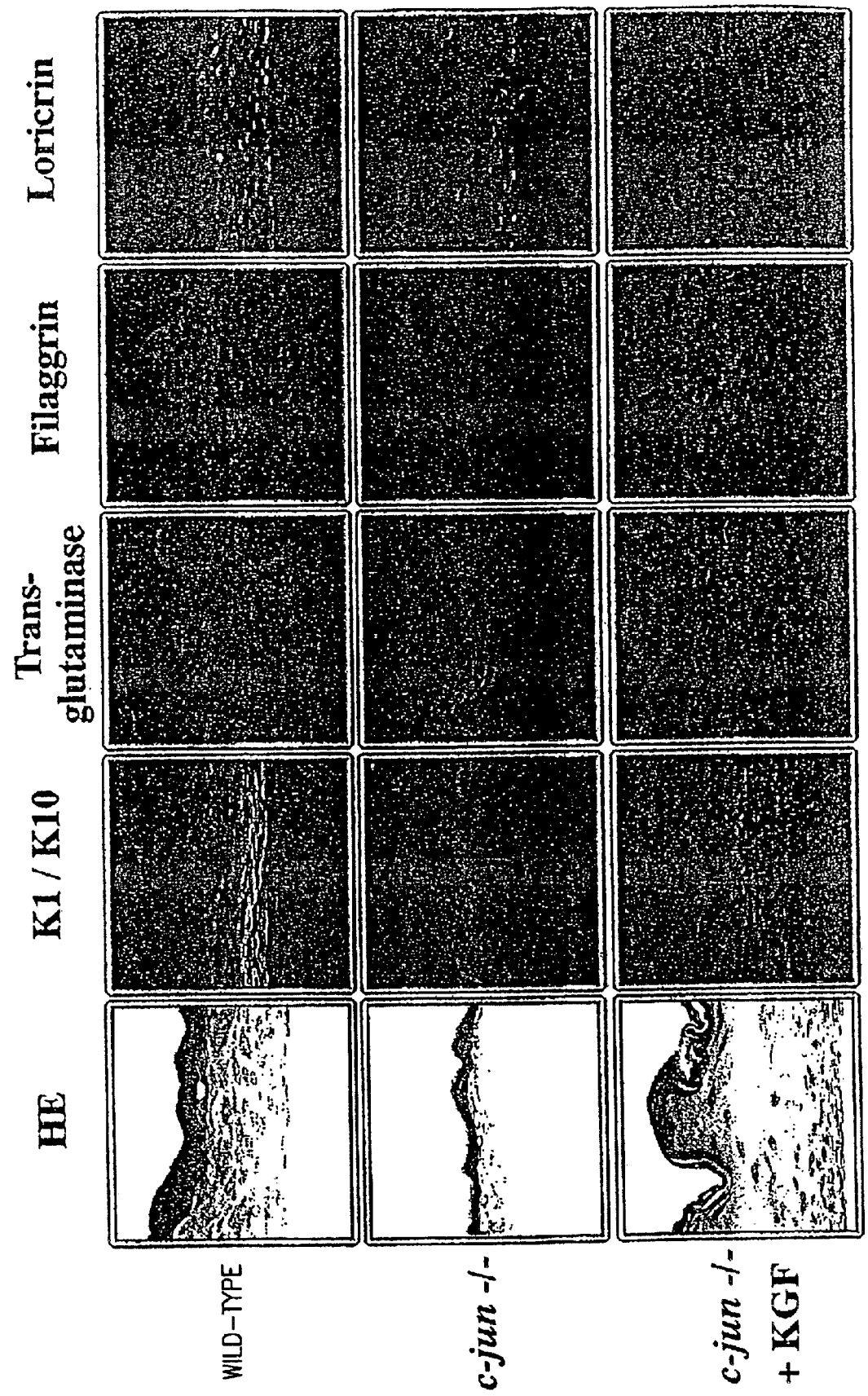
Figure 6B:
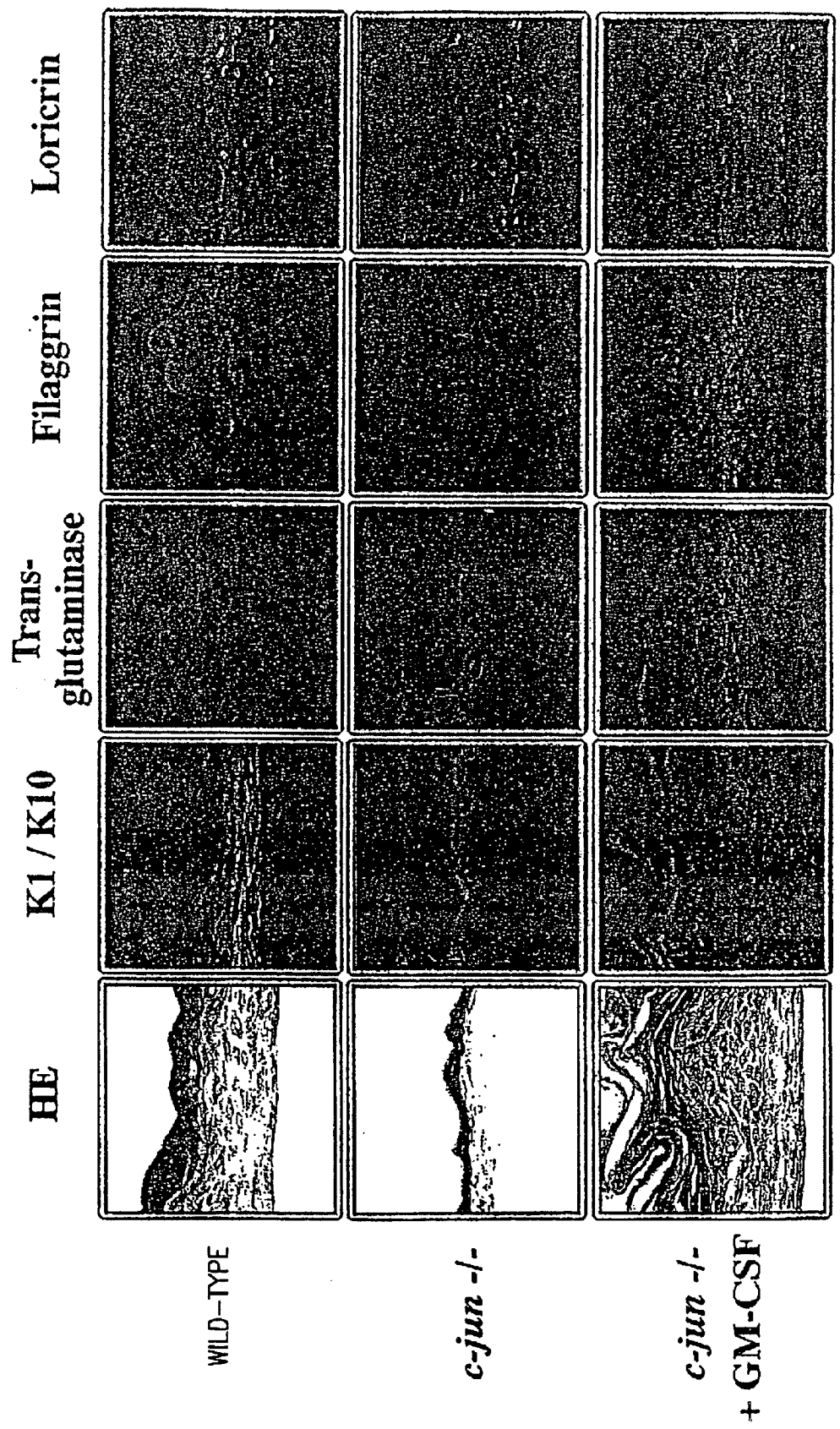

Basically skin-specific genes indicating a certain differentiation type are in consideration as marker genes. The genes used in FIGS. 4–6 represent usable markers. The expression is determined by in situ hybridization or preferably immunohistochemistry (IHC) or immunofluorescence. The criteria for proliferation and differentiation are both histological criteria (e.g. thickness of the epithelium) and the expression strength -and localization of the marker genes ki-67 (proliferation) and of the genes used in FIGS. 4–6 (differentiation).

Changes in the expression level of the marker gene can be studied using methods well known to a person skilled in the art. They comprise the monitoring of the mRNA concentration (e.g. using suitable probes or primers), immunoassays as regards the protein concentration (e.g. by means of corresponding antibodies), RNAse protection assays, amplification assays or any other means suitable for detection and known in the art.

New compounds whose expression is regulated directly or indirectly by AP-1 or which regulate the proliferation and/or differentiation of skin keratinocytes and are thus of therapeutic value, can also be searched for on a large scale, e.g. by screening a very large number of candidate compounds in substance libraries, the substance libraries being able to contain synthetic or natural molecules.

The above method according to the invention can be modified by means of protocols described in the scientific literature and patent literature and known in the art. For example, a large number of possibly useful molecules can be screened in a single test. For example, when a field of 1000 compounds shall be screened, in principle all of the 1000 compounds can be placed in a microtitration plate well and tested at the same time. When the presence of a compound having the desired activity is discovered, the pool of 1000 can be divided into 10 pools of 100 and the process can be repeated until an individual compound is identified. In any case, the production and simultaneous screening of large libraries from synthetic molecules can be carried out by means of well known methods of combinatorial chemistry, see e.g. van Breemen, 1997, and Lam, 1997.

The method according to the invention can also be accelerated greatly as high throughput screening. The assays described herein can be modified correspondingly so that they can be used in such a method. It is obvious to the person skilled in the art that a number of methods are available for this purpose.

By means of the method according to the invention the molecular modes of action of cytokines, for example, can be studied as to the growth and differentiation processes of the skin.

The present invention also relates to a method of identifying a gene involved in the AP-1-dependent differentiation and/or proliferation of keratinozyctes. Here, the expression pattern of genes in standard fibroblasts and genetically modified fibroblasts, such as c-Jun–/– and JunB–/– cells, is compared. Genes regulated differently are potential candidates for genes regulating the proliferation and differentiation in keratinozcytes. The c-Jun–/– cell line which carries the Ubi-cJun-ER™ expression vector and/or the JunB–/– cell line which carries the Ubi-JunB-ER™ expression vector is preferably used for comparative gene expression analysis. Here, the expression in untreated and tamoxifen-treated cells shall be compared. In all of the cases, RNA is prepared from the corresponding cells and transcribed into cDNA. The cDNA can in this connection be labeled either radioactively or by a fluorescent dye. The cDNAs serve as probes for the hybridization of filters or glass carriers on which a plurality of indicative sequences of individual genes are immobilized. Genes whose expression changes under the above described-conditions can be identified by means of the differences in the hybridization strength. This comparative gene expression analysis by means of "high density filter screening" and "DNA chip technology" are described in Iyer et al. (1999) and Fambrough et al. (1999). In known genes, the corresponding substance may either be added directly to the culture medium as recombinant protein (e.g. in the case of a cytokine or growth factor) or be inserted by means of gene transfer in the modified fibroblasts and expressed. The same applies correspondingly for DNA sequences unknown thus far.

In a particularly preferred embodiment of the method according to the invention, the marker gene is a gene coding for K1/K10, transglutaminase, filaggrin or loricrin (Stark et al., 1999). The expression of these genes can be determined in accordance with the above statements, e.g. also in accordance with the methods described in below Examples 11 to 13, using suitable antibodies.

A compound identified by the method according to the invention or an identified gene can then be used for treating diseases, the expression of the target gene being reduced or eliminated depending on the kind of disease (e.g. by knocking out the gene in the target cell or by blocking the translation via antisense RNAs or ribozymes or via vectors containing polynucleotides as insertions, which code for antisense RNAs or ribozymes) or being increased, e.g. by administering a vector containing the target gene under the control of a suitable promoter, e.g. an inducible promoter or a promoter resulting in an intensive expression. This vector may be derived from a virus, e.g. from an adeno-associated virus (e.g. AAV type 2), vaccinia virus or adenovirus which is of use for a gene therapy. Retroviruses are particularly preferred. Examples of suitable retroviruses are MoMuLV, HaMuSV, MuMTV, RSV or GaLV. Methods of producing suitable vectors based on the above viruses are known to the person skilled in the art. The genes or the vectors containing them can also be transported to the target cells in the form of colloidal dispersions for the purpose of gene therapy. They comprise liposomes or lipoplexes, for example. Antibodies directed against proteins encoded by the above genes and preferably having a neutralizing effect are also suited for a therapy. These antibodies may be monoclonal, polyclonal or synthetic antibodies or fragments thereof. In this connection, the term "fragment" refers to all parts of the monoclonal antibody (e.g. Fab, Fv or single chain Fv fragments) which have an epitope specificity the same as that of the complete antibody. The production of such fragments is known to the person skilled in the art. The antibodies according to the invention are preferably monoclonal antibodies. The antibodies according to the invention can be produced according to standard methods, the protein encoded by the genes to be studied or a synthetic fragment thereof preferably serving as an immunogen. Methods of obtaining monoclonal antibodies are also known to the person skilled in the art. When the substances, genes or antibodies identified according to the method of the invention are administered, they are preferably available in combination with a pharmaceutically compatible carrier. Suitable carriers are e.g. phosphate-buffered common salt solutions, water, emulsions, e.g. oil/water emulsions, wetting agents, sterile solutions, etc.

The medicaments containing these substances can be administered orally or preferably parenterally. The methods of parenteral administration comprise the topical, intra-arterial, intramuscular, subcutaneous, intramedullary, intrathekal, intraventricular, intravenous, intraperitoneal or intranasal administration. The suitable dose is determined by the attending physician and depends on various factors, e.g. on the patient's age, sex and weight, the stage of the disease, e.g. the skin tumor, the kind of administration, etc.

Thus, the present invention also relates to the use of the compound identified according to the method of the invention, the gene or antibody directed against a protein encoded by this gene for treating diseases associated with a disturbed proliferation and/or differentiation of keratinocytes, preferably skin diseases, such as psoriasis, chronic inflammations of the skin, delayed wound healing or skin tumors. Furthermore, acne, neurodermatitis, eczemas and scar treatment should be mentioned. Two examples of antibodies whose desired properties can be identified in test systems I and II (FIG. 7) are those directed against interleukin 1 and GM-CSF and neutralize the activity of these cytokines. Likewise compounds can be identified by means of the present invention, which relate to the proliferation and differentiation of various epithelia or disturbances which are accompanied by corresponding diseases and are likewise controlled via interactions with the associated connective tissue cells. The identified compounds can then be tested in corresponding coculture models as to their relevancy. Corresponding models are available or under development for oral mucosa, liver, mammary gland, prostate/urinary bladder, intestine.

Finally, the present invention relates to the use of the gene identified according to the method of the invention or a fragment thereof or an antibody against the protein encoded by this gene for the diagnosis of diseases associated with a disturbed proliferation and/or differentiation of keratinocytes. Here, a suitable tissue sample is withdrawn according to methods known to the person skilled in the art and the diagnostic detection is carried out in accordance with the probe used, e.g. as a Southern blot, Northern blot, PCR, sequencing or as immunohistochemical or immunological detection, e.g. as RIA or ELISA. As to the expression "antibody" reference is made to the above definition.

The above described preferred embodiments of the system according to the invention have the advantage that, on the one hand, the actual direct target genes, e.g. of c-Jun or Jun-B, can be detected by this, since there is a defined starting point of activity (e.g. addition of hormone). On the other hand, a large amount of active protein is immediately available, which represents an advantage over vector systems based on an inducible promoter (in this case the protein amount can only be raised by neosynthesis in the course of several hours). Clonal differences between the cell lines can also be ruled out in the system according to the invention.

Figure 1B:
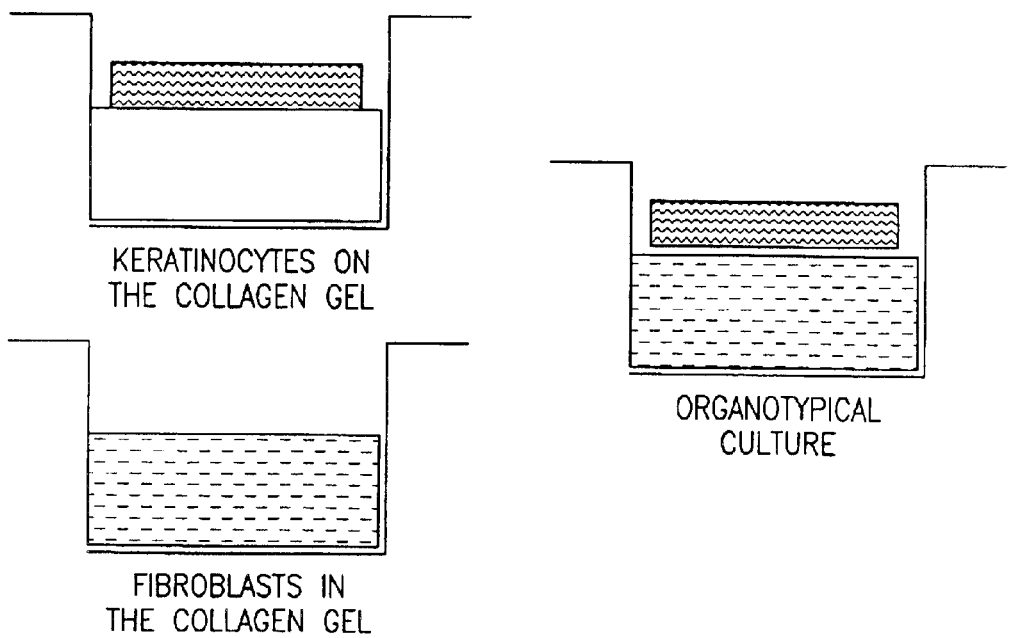

The figures show:

FIG. 1: Diagram of the coculture system and organotypical culture system (A) Diagram of the monolayer culture on plastic surfaces. The primary keratinocytes can be cultured at a great dilution only in the presence of a feeder layer from fibroblasts. (B) structure of an organotypical culture. The principle of coculturing fibroblasts and keratinocytes is expanded by two points: i) comparable to the natural skin the fibroblasts grow in a collagen matrix, and ii) the keratinocytes grow here on this matrix while exposed to air.

Figure 2A:
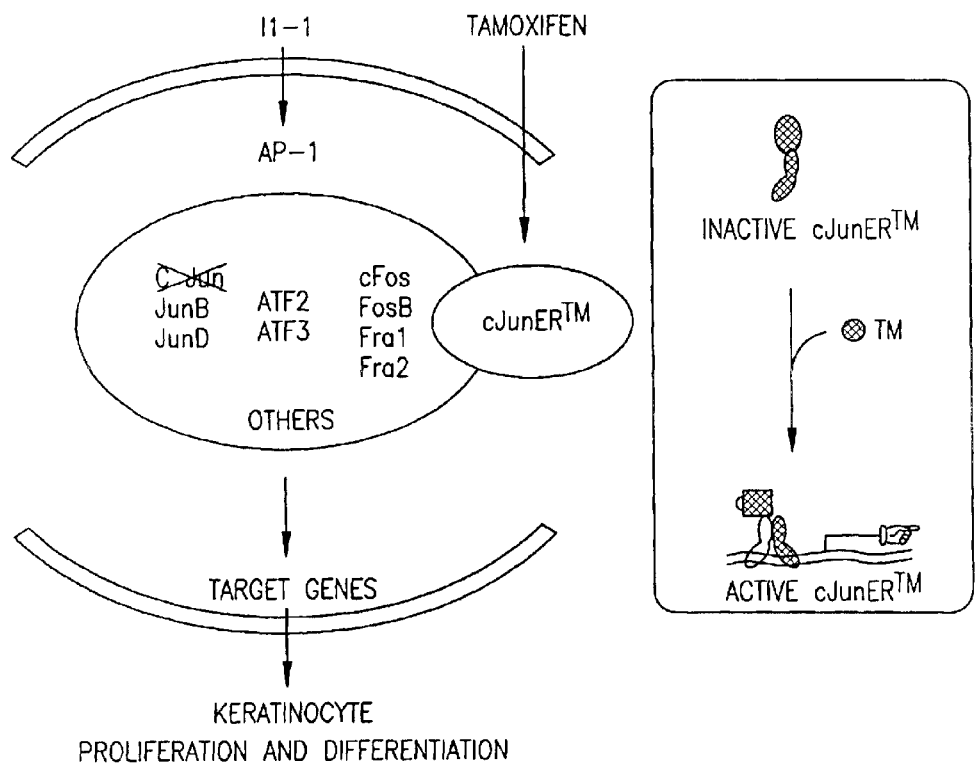
Figure 2B:
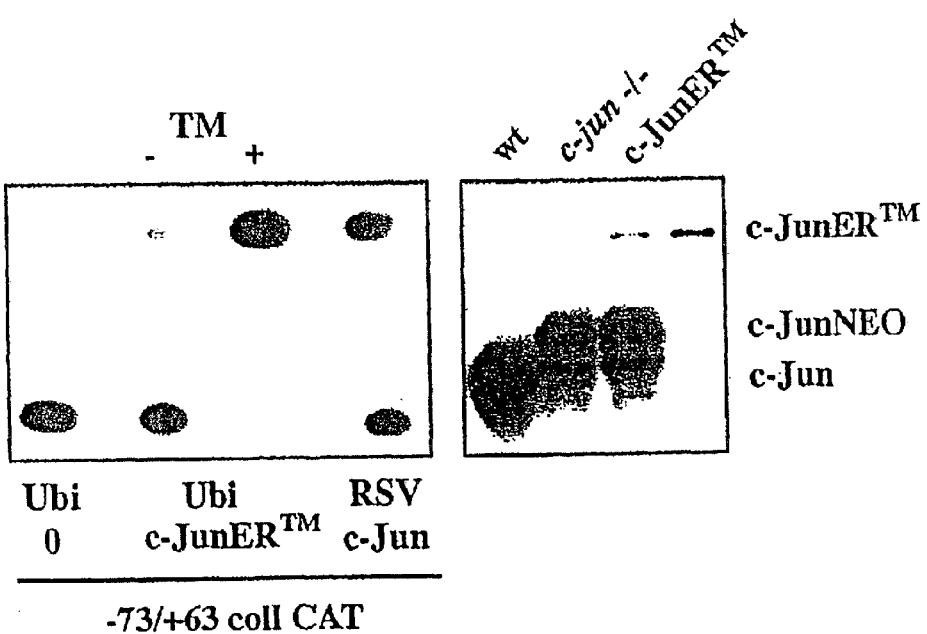

FIG. 2: Diagram of the properties of the c-jun–/– e-JunER™ fibroblasts

The endogenous AP-1 member c-Jun is no longer expressed functionally in the fibroblasts (c-Jun –/–). The fusion protein c-JunER™ introduced into the cells can adopt the function of the lacking c-Jun protein when it is activated by exogenous addition of the ligand 4-OH-tamoxifen. This operating principle of the fusion protein c-JunER™ is based on the fact that the c-Jun part of the protein is inactivated as long as no ligand is bound to the modified estrogen receptor binding domain (ER™). The c-Jun part of the fusion protein can only dimerize after the binding of the ligand by ligand-induced conformational change with other AP-1 members and fulfill its transactivating function. The CAT assay shows that by adding 100 nM 4-OH tramoxifen the c-JunER™ fusion protein can induce the expression of the transiently transfected reporter gene chloramphenicol-acetyl transferase (CAT) which is controlled by the classical TRE (TPA response element) from the collagenase gene. The Western blot confirms that the stably transfected c-jun –/– fibroblasts express the fusion protein c-JunER™.

Figure 3:
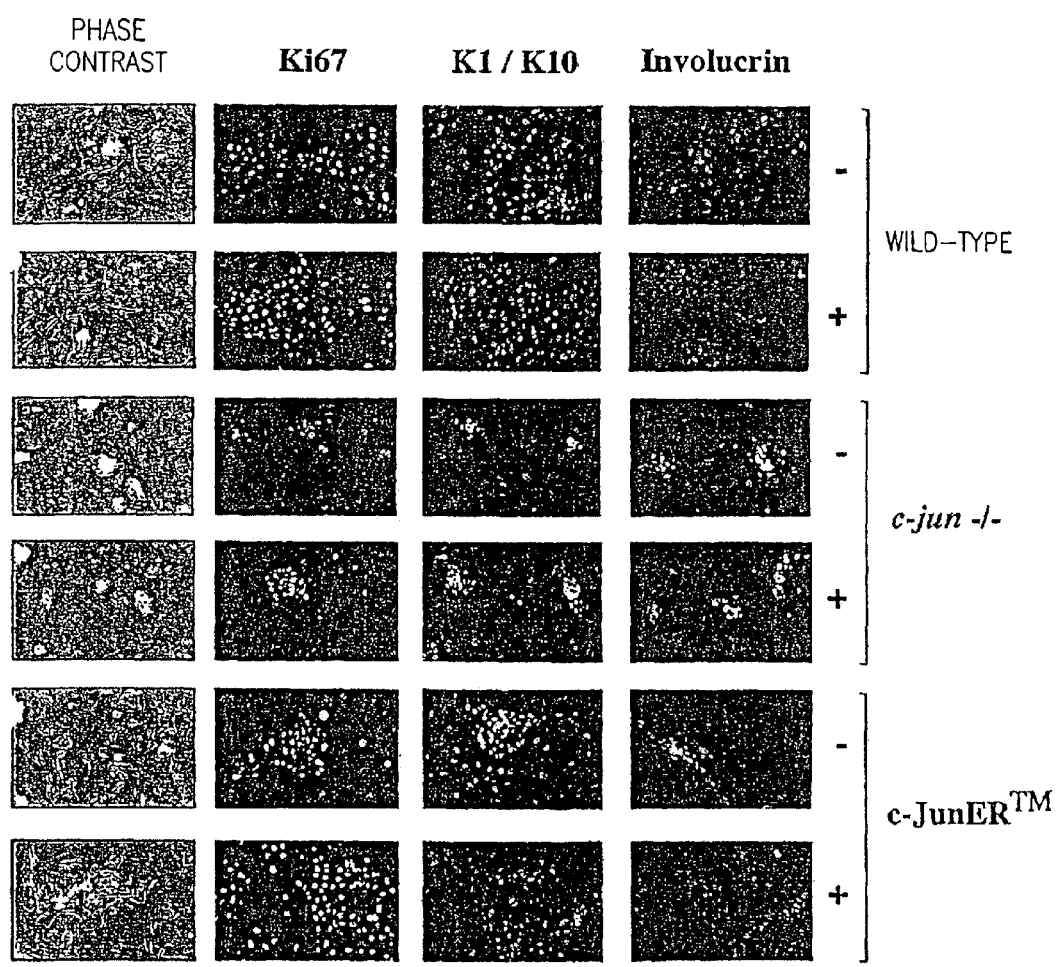

FIG. 3: Wild-type, c-jun –/– and c-jun –/– c-JunER™ fibroblasts in coculture with primary human keratinocytes The proliferation and differentiation in fibroblasts is effected inter alia by c-Jun activity.

FIG. 4: Characteristics of the in vitro organotypical cultures

The organotypcial coculture system as a model for the proliferation and differentiation in skin FIG. 5: Comparison of organotypical cultures with murine wild-type 3T3 fibroblasts and c-jun-deficient or JunB-deficient fibroblasts FIG. 6: The phenotype obtained in organotypical cultures with c-jun –/– can partially be reversed by adding KGF (A) or GM-CSF (B)

Figure 7:
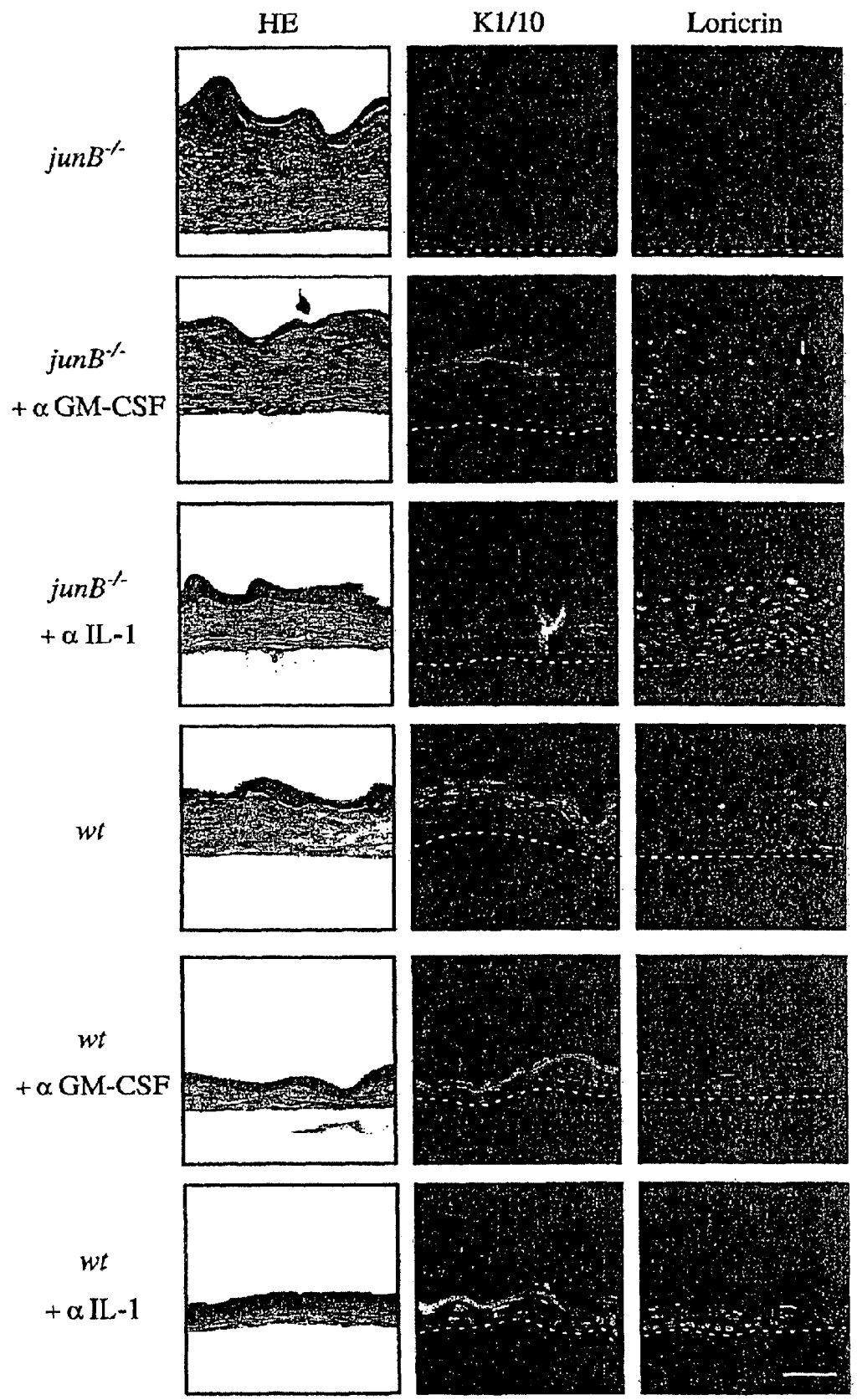

FIG. 7: The epithelial formation in organotypical cultures with wt and junB –/– MEF can be changed by adding neutralizing antibodies The "atypical" epithelial formation obtained in organotypical cultures with junB –/– MEF (murine embryonal fibroblasts) can partially be normalized by adding GM-CSF-neutralizing and IL-1-neutralizing antibodies. As can be seen, the application of the neutralizing antibodies (α IL-1 or α GM-CSF) reduces hyperproliferation and normalizes the differentiation state of the epithelium in organotypical cultures with junB –/– MEF. These changes can be seen histologically by the normalization of the grnaular layer and the expression of the differentiation marker, loricrin. In organotypical cultures with wt MEF, it is possible to greatly reduce the epithelium formation by adding GM-CSFneutralizing and IL-1-neutralizing antibodies. These changes can be seen histologically by the reduction of the epithelial thickness and the reduced expression of the differentiation marker, loricrin.

The following examples explain the invention.

EXAMPLE 1

Isolation of Primary Fibroblasts of Wild-type and JunB−/− Embryos; Establishment of Immortal Cell Lines Primary murine embryonic fibroblasts (MEF) were isolated according to the method by Todaro and Green (1963) and immortalized. For the preparation of primary fibroblasts mouse embryos were obtained from the uterus on days 9.5 and 10.0 of the embryonic development from heterocygously paired junB +/− females (Schorpp-Kistner et al., 1999) after killing them by cervical dislocation. The embryos were isolated in PBS from the maternal decidua. Having removed the extraembryonic tissue and the amnion used for genotyping, the corpus was comminuted in DMEM medium (with 10% FCS, penicillin/streptomycin 1%, 1 mM L-glutamine) into small tissue fragments and cell groups by sucking it up into sterile 2.5 ml disposable syringes having 25 G canulas. These tissue fragments and cell accumulations were seeded onto a six-well cell culture plate and cultured in DMEM medium having the above composition in an incubator. The following day, non-adhered coarse tissue fragments were removed by washing using PBS and the adhered primary fibroblasts were continued culturing after giving new DMEM medium. After 5 and 7 days (embryos of day 10.0 and 9.5, respectively), the cells were passaged by trypsination and plated onto three T25 cell culture bottles with a density of about $3\times10^5$ each (Greiner company, Frickenhausen, Germany). These MEF were passaged every three days and seeded with a cell density of $1-3\times10^4$ cell per $cm^2$. From passages 7 to 16, the exponential growth was concluded by what is called a crises. During this crisis the cells were allowed to stay on the cell culture dish without trypsination for 7 to a maximum of 17 days. The cells were observed, and the medium was changed every 3 days. As soon as another cell increase was observed, the cells were again trypsinized every 3 days and seeded with a cell number of $3\times10^4$ per $cm^2$. By constant further passing, immortalized cell lines formed after 16 to 18 passages, which were cryopreserved or used for subsequent experiments. The immortalized cells were again examined as to their genotype. This genotyping as made as described by Schorpp-Kistner et al., 1999.

EXAMPLE 2

Isolation and Culturing of Primary Human Keratinocytes and Fibroblasts

Epidermal keratinocytes and dermal fibroblasts were isolated from biopsies of human body skin (Boukamp et al., 1990). Keratinocytes were cultured as feeder-layer cocultures in FAD medium (DMEM:Hams F12/3:1 (Sigma company, Deisenhofen, Germany) with 0.1% glucose, 1 mM L-glutamine; pH 7.3; with 100 U/ml penicillin, 10 μg/ml streptomcyin, 5 μg/ml insulin, 1 ng/ml hEGF, $10^{-10}$ M cholera toxin, 24 ng/ml adenine (all additions from Sigma, Deisenhofen, Germany; with 5% FCS) ($1\times10^4/cm^2$ feeder cells and $1.1\times10^4/cm^2$ keratinocytes). Human fibroblasts were multiplied in DMEM with 10% FCS. For the production of feeder fibroblasts, human fibroblasts with 70 gray and mouse fibroblasts were irradiated with 20 Gy. The activation of the c-Jun-ER fusion protein in the stable c-jun−/− cell line which contains an inducible c-Jun-ER™ expression vector, was made by adding 4-OH-tamoxifen (Sigma) to the culture medium (final concentration 100 nM). Corresponding steps were taken to activate the JunB-ER™ fusion protein.

EXAMPLE 3

Organotypical Cultures

Type 1 collagen was prepared from rat tail tendons and provided at a concentration of 4 mg/ml in 0.1% acetic acid as rdady-to-use solution (Smola et al., 1993). The collagen gels used consisted of 80% by volume of 4 mg/ml collagen in 0.1% acetic acid, 10% by volume Hank's salt solution (concentrated tenfold) and 10% by volume FCS with or without cells ($2\times10^5$ cells/ml). The liquid collagen was admixed with Hank's solution on ice and neutralized with 5 M NaOH with stirring (trypsinated cells taken up in FCS can then be added to the collagen solution by stirring). The gel solution was poured into cell culture dishes or 2.5 ml each into filter inserts (3 μm pore size, Becton Dickinson, Heidelberg, Germany) and allowed to stay in an incubator to form a gel for 1 hour. Sterile glass rings having an internal diameter of 18 mm (1.5 mm wall thickness, 12 mm height) were placed onto the gels and slightly pressed thereon. Following 1 h in the incubator, the collagen gels were equilibrated in DMEM with 10% FCS. After 24 h, the medium was withdrawn from the glass rings and 1 ml keratinocyte suspension ($9\times10^5$ cells/ml FAD) each were seeded into the glass ring interior. After 24 h of incubation, the medium was removed from the keratinocytes so as to expose the cells to air. This time was defined as day 0 of the organotypcial cultures. DMEM having 10% FCS was exchanged every other day, the medium level in this case bordering on the top gel rim. For histological or immunohistochemical processing, the cultures were fixed or frozen. In order to detect proliferating cells in a culture by immunohistochemical methods, the cultures BrdU (Sigma) were added to the medium at a concentration of 65 μM 12 h prior to fixing.

EXAMPLE 4

Application of Cytokines 2D cocultures on plastic dishes or glass slides or in 3D form as organotypical cultures were incubated in corresponding standard medium for 24 h. Thereafter, medium enriched with cytokines was added and the cultures were incubated therewith depending on the experiment for several hours or days, the medium being changed with factor added every other day. Supplier of the growth factors and antibodies: KGF (BTS, St. Leon, Germany); anti-GM-CSF, polyclonal, neutralizing (R&D-Systems, Wiesbaden, Germany); GM-CSF (Boehringer Mannheim, Germany) and anti-KGF, monoclonal, neutralizing (R&D-Systems).

EXAMPLE 5

Fixing of Cultures

In the case of monolayer cultures of adherent cells, the medium was withdrawn from the cells and the cells were fixed on the glass slides in 80% methanol for 5 min. and 100% acetone for 3 min. The slides were then dried and stored at −40° C. For the production of paraffin preparations, organotypical cocultures or skin biopsies wee fixed in 3.5% formaldehyde (in PBS+) for at least 24 h, and initially embedded in agar and then in paraffin (Medim, Vogel company, Gießen, Germany). The preparations were cut into 2 µm sections which were stained histologically with hematoxylin (15 min.) and eosin (5 min.). Following deparaffinization it was also possible to use the paraffin sections for immunohistochemical analyses. For the production of frozen preparations, skin samples or organotypical cocultures were frozen on cork platelets in embedding gel ("Tissue Teck", O.C.T., Frankfurt, Germany) on liquid nitrogen. The preparations were stored at −80° C. 5-µm sections were prepared using a freezing microtome, placed onto silanized slides and used for immunohistochemical analyses.

EXAMPLE 6

Immunohistochemical Analyses

Paraffin sections were deparaffinized in a descending alcohol series and rinsed in PBS. Thereafter, the epitopes on the tissue sections were made accessible by boiling the sections in "Tuf" solution for 5 min. (Advanced Biotechnologies, Hamburg, Germany) and 0.1% trypsin at 37° C. or microwave treatment in 0.1 M citrate buffer for 30 min. Freeze sections were fixed in 80% methanol for 5 min., then in acetone for 2 min. For detecting the incorporation of BrdU (proliferation assay), the sections were incubated in 1.5 M HCl for 10 min. to denature the DNA strands. The first antibody, diluted in 1% BSA solution, was incubated at 37° C. for 1 h or at 4° C. for 12 h. Following three washings in PBS+, the second fluorochrome-coupled antibody was applied at room temperature for 45 min. The second antibodies against IgG mouse or IgG rabbit were coupled as chosen with FITC (green) or "Texas red" (red) (Dianova, Hamburg, Germany). To stain the nucleus, the DNA dye, bisbenzimide, (Dianova, Hamburg, Germany) was added to the second antibody at a final concentration of 5 ng/ml. Excess antibodies were removed by washing (3×for 10 min., PBS+) and the sections were covered with "Mowiol" (O.C.T., Frankfurt, Germany) and a cover glass. The following antibodies were used:

$1^{st}$ antibodies against BrdU (specificity: mouse) from Dianova, Hamburg, Germany; $1^{st}$ antibodies against filaggrin (specificity: mouse) from Cell Systems, St. Katharina, Germany; antibodies against K10 (clone 8.60) (specificity: mouse) from Sigma, Deisenhofen, Germany; antibodies against loricrin (specificity: rabbit) from D. Hohl, Lausanne, Switzerland; antibodies against Ki-67 (Mib-1) (specificity: mouse) from Calbiochem, Bad Soden, Germany; antibodies against transglutaminase (specificity: mouse) form Cell Systems, St. Katharina, Germany.

EXAMPLE 7

Reverse Transcription Polymerase Chain Reaction (RT-PCR)

Whole RNA was prepared according to the protocol from Chomczynski and Sacchi, 1987 (see Schorpp-Kistner et al., 1999) and transcribed into cDNA in the following batch: 10 µg RNA, 10 µl 10×PCR buffer, 20 µl 25 mM $MgCl_2$, 6 µl of each dNTP (10 mM each), 2.5 µl RNase inhibitor (20 U/µl), 5 µl 50 U/µl MLV reverse transcriptase, 2 µl 50 µM Oligo-$dT_{16}$, 2 µl 50 µM "random hexamer" primers and $H_2O_{depc}$ until a whole volume of 100 µl has been reached. The reaction batches incubated at room temperature for 10 min., the at 42° C. for 80 min. and were stopped by heating for 5 min. to 95° C. 5 µg whole RNA were transcribed into cDNA correspondingly in a 50 µl batch and the resulting products were stored at −20° C.

All of the following PCR steps were matched with the use of the products of the "PCR Core" kit from Boehringer Mannheim and the "TrioThermoblock" from Biometra company, Göttingen, Germany. 4 µl of the reverse transcription batch were used each. The following were added to a whole volume of 50 µl: 1×PCR buffer, 200 µM of the deoxynucleotides each, 0.2 µM of each primer, depending on the amplification conditions 1.5 mM to 2.5 mM $MgCl_2$ and 1.5U Taq polymerase. 50 µl mineral oil (Sigma) were added dropwise to each batch to avoid evaporation of the reaction mixture during the PCR reaction. The first cycle of PCR comprised denaturation of the matrix at 94° C. for 5 minutes. This was followed by 20 to 30 cycles (denaturation at 94° C. for 1 min., hybridization at primer-specific temperature for 1 min., synthesis by the Taq polymerase at 72° C. for 1 min.) corresponding to the linear amplification region for the select fragment. PCR was concluded with a synthesis at 72° C. for 5 minutes to complete incompletely synthesized fragments. The batches were stored at −20° C. until they were further used.

EXAMPLE 8

Production and Analysis of the c-jun −/− Cell Lines Stably Containing a c-Jun-ER™ Expression Vector For subcloning the c-JunER™ DNA fragment, the AccI/SalI restriction site was removed from the multiple cloning site of a "Bluescript SK" vector (Stratagene company, La Jolla, U.S.A.). For this purpose, the vector was linearized using HincII, EcoRI linkers were added to the vector by ligation, and following restriction religation was carried out using EcoRI. The c-JunER™ DNA fragment was isolated by means of EcoRI digestion from PMV7 c-JunER™ (Bossy-Wetzel et al., 1997) and subcloned into the EcoRI restriction site of the modified "pBluescriptSK" vector. For exchanging part of the murine c-Jun sequence, the vector was digested with AccI/HapI and replaced by the equivalent AccI/HapI fragment of the human c-Jun sequence (Angel et al., 1988). The resulting c-JunER™ hybrid from murine and human sequences was subcloned into an unmodified "pBluescript" vector by means of EcoRI digestion. To optimize the expression of the fusion protein, the c-Jun-ER sequences were controlled by the human ubiquitin-C promoter/enhancer sequence already identified as very efficient regulation unit in transgenic mice (Schorpp et al., 1996). For this purpose, part of the c-JunER™ was isolated as SalI/NcoI fragment from the vector and used in a SalI/NcoI-cleaved "Ubi JunB ER™" vector (Schorpp et al., 1996). The c-jun −/− fibroblasts were cotransfected by means of lipofection (Lipofectamin, Gibco BRL, Karlsruhe, Germany) in accordance with the manufacturer's protocol using 1.6 µg "Ubi c-JunER™" and 0.4 µg "pSV Hygro" (expression vector for the hygromycin resistance gene; expression is regulated via the promoter/enhancer region of SV40).

After 3 weeks of growing on selection medium (DMEM with 10% FCS and 50 µg/ml hygromycin B), clonal colonies were isolated and expanded. The genomic DNA of the fibroblasts were isolated by means of standard protocol. Genotyping was carried out by means of PCR. PCR machine: PTC-2000 from Biozyme Diagnostic (GmbH, Hess. Oldendorf Germany; reaction conditions: 50 ng genomic DNA 5 mM $MgCl_2$, 10% DMSO, 1×GB buffer (16.6 mM $(NH_4)_2SO_4$; 6.7 mM $MgCl_2$; 5 mM β-mercaptoethanol; 6.7 mM EDTA), 0.5 mM dNTPs, 35 ng PCR primer (5' primer: 5'atgaggaaccgcattgcg (SEQ ID NO1); 3' primer: 5'-tggagattcaagtccccaaagcc (SEQ ID NO:2)) and 1 unit Taq polymerase (Sigma). PCR program: 5' 94° C.; 35×(94° C. 45"; 55° C. 1'; 72° C. 1'); 7' 72° C. Genotypically positive clones were checked by means of Western blot (□-cJun/AP-1 monoclonal mouse antibodies from Signal Transduction Laboratories, Dianova, Hamburg, Germany) for expression of the fusion protein c-JunER™. Gene expression (Northern blot, RT-PCR) and protein amounts (Western blot, ELISA) were detected according to current standard protocols.

EXAMPLE 9

Production and Analysis of the JunB −/− Cell Lines Stably Containing an Ubi-JunB-ER™ Expression Vector For the production of a junB-ER™ expression vector, the stop codon was initially replaced in junB by means of a DNA fragment consisting of 2 oligonucleotides (sequence oligo1: 5'-acggctgccagttcggctaggggtcaagggacacgccttc-3' (SEQ ID NO:3'); oligo2: 5'-gtctggactcgaggatccccgaaggcgtgtcccttgaccc-3' (SEQ ID NO:4)) in a 3' subclone of junB (323 base pairs BssHii-XhoI fragment between restriction sites AlwNI and XhoI). The complete junB cDNA fragment was excised from Ubi junB (Schorpp et al., 1996) using SmaI, provided with EcoRI linkers and cloned into the EcoRI restriction site of pBluescript SK (Stratagene, La Jolla, U.S.A.). The final junB-ER™ construct was prepared by ligation from the following 4 fragments: 5' region: EcoRI/BspHI fragment from the complete junB cDNA in pBluescript SK; 3' region with the replaced stop codon: BspHI/BamHI fragment; BamHI/EcoRI ER™ fragment from PMV7 c-jun-ER™ (Bossy-Wetzel et al., 1997); EcoRI-cleaved pBluescript SK. The resulting junB-ER™ fragment was isolated as XbaI/SalI fragment and inserted in an XbaI/XhoI-cleaved Ubi junB expression vector (Schorpp et al., 1996). The junB −/− fibroblasts were cotransfected by means of lipofection (lipofectamin; Gibco BRL, Karlsruhe) in accordance with the manufacturer's protocol with 2.8 µg Ubi junB-ER™ and 0.4 µg pSV hygro. After 3 weeks on selection medium (DMEM) with 10% FCS and 50 µg/ml hygromycin B), clonal colonies were isolated and expanded. The genomic DNA of the fibroblasts was isolated by means of a standard protocol. Genotyping was made by means of PCR. PCR was carried out in a thermocycler PTC 200 from Biozym (Hess. Qidendorf) with the following reaction conditions: 50 ng genomic DNA, 2.5 mM $MgCl_2$, 10% DMSO, 1×GB buffer (16.6 mM $(NH_4)_2SO_4$, 6.7 mM $MgCl_2$, 5 mM beta-mercaptoethanol, 6.7 µM EDTA), 0.5 mM dNTPs, 20 ng PCR primer (5' primer: 5'-cagaccgtaccggaggcacgcagc-3' (SEQ ID NO:5'), 3' primer: 5'-tggagattcaagtccccaaagcc-3' (SEQ ID NO:6)) and 1 unit Taq polymerase (Sigma, Deisenhofen); program: 2' 94° C.; 30×(30" 94° C., 90" 55° C., 2' 72° C.); 10' 72° C. Genotypically positive clones were checked by mean of Western blot analysis with a polyclonal antibody from rabbit against junB (N17, Santa Cruz Heidelberg) for expression of the fusion protein junB-ER™. Gene expression (Northern blot, RT-PCR) and the protein amounts (Western blot, ELISA) were detected according to common standard protocols.

EXAMPLE 10

Wild-Type, c-jun −/− and c-jun −/− c-JunER™ Fibroblasts in the 2D Coculture with Primary Human Keratinocytes A coculture of fibroblasts and keratinocytes was analyzed by means of a light microscope and by means of immunofluorescence (IF) for proliferation and differentiation of the keratinocytes after three days (FIG. 3). 100 nM 4-OH tamoxifen wee added to the cultures every 12 hours and the medium was exchanged every 24 hours. The corresponding controls remained untreated. In IF, the cell nuclei were made visible by the Hoechst dye bisbenzimide (blue staining). The keratinozcyte islet size (detectable in the phase contrast and by involucrin staining) is markedly reduced by the lack of c-Jun activity. Less proliferating keratinocytes (staining for Ki67) are also detectable. The expression of the differentiaton marker K1/K10 (green staining) is enhanced. It can be eliminated again in the c-jun −/− c-JunER™ fibroblasts by tamoxifen-induced c-Jun activity.

EXAMPLE 11

Characteristics of the In Vitro 3D-Organotypical Cultures

Comparison of human skin with seven-day-old organotypical cultures in which primary human fibroblasts and murine 3T3 fibroblasts were used (FIG. 4). It demonstrates that due to the organotypical cultures an in vitro system is available which is equivalent both histologically and with respect to the expression of marker genes of the normal human skin. The expression of the genes K1/K10, transglutanminase, filaggrin and loricrin are generally recognized as marker genes for the differentiation state of the keratinocytes. Normal epithelia form with both human and murine fibroblasts. Thus, it is obvious that the molecular mechanisms controlling epithelial formation are conserved in species-embracing fashion between humans and mice.

EXAMPLE 12

Comparison of Organotypical Cultures with Mouse-wild-type 3T3 Fibroblasts and c-jun-deficient or JunB-deficient Fibroblasts Contrary to wild-type mouse 3T3 fibroblasts, c-jun-deficient or junB-deficient fibroblasts induce a modified epithelial structure in organotypical cultures (FIG. 5). These abnormal epithelia are characterized by inhibiting or stimulating proliferation, resulting in a decrease or increase in the epithelial thickness and by a modified differentiation. The organotypical cultures obtained with c-jun −/− fibroblasts show a markedly reduced proliferation and epithelial formation, and the expression of the late differentiation markers filaggrin and loricrin is also drastically reduced. The epithelium of the organotypical culture with junB −/− fibroblasts is thickened and shows highly increased proliferation and a modified differentiation both histologically and by means of IF. The expression of the K1/K10 marker starts late and can only be detected in higher cell layers. The differentiation markers transglutaminase, filaggrin and loricrin are enhanced and in the case of loricrin also expresseed prematurely.

EXAMPLE 13

The Phenotype Obtained in Organotypical Cultures with c-jun −/− can Partially be Reversed by Adding KGF or GM-CSF The application of the cytokines KGF or GM-CSF to the organotyp nical cultures with c-jun −/− fibroblasts eliminates the reduced epithelial formation. However, by KGF administration (FIG. 6A) the full differentiation status is not restored. This is histologically detectable by lack of the granular layer and the expression of the differentiation markers filaggrin and loricrin. Although the addition of the cytokine GM-CSF (FIG. 6B) effects an enhanced epithelial formation, in this case the differentiation state of the epithelium does not correspond to the normal condition. K1/K10 is expressed late and transglutaminase, filaggrin and loricrin are expressed enhancedly and loricrin is expressed prematurely.

The following cell cultures were deposited with DMSZ (*Deutsche Sammlung von Mikroorganismen und Zellkulturen GmbH* [German-type collection of micro-organisms and cell cultures], Mascheroder Weg 1b, Braunschweig, Germany) in accordance with the provisions of the Budapest Treaty:

| On Nov. 11, 1999: | |
|---|---|
| Cell culture 10JunB-/- | DSM ACC2419 |
| On Dec. 21, 1999: | |
| Cell culture 55/2c-Jun-ER ™ wt#180 | DSM ACC2438 |
| Cell culture 10JunB-ER ™ #7 | DSM ACC2439 |

Reference List

Angel, P., Allegretto, E. A., Okino, S., Hattori, K., Boyle, W. J., Hunter, T. and Karin, M. (1988). Oncogene Jun encodes a sequence specific trans-activator similar to AP1. Nature 332: 166–171.

Angel, P. and M. Karin (1991), The role of Jun, Fos and the AP-1 complex in cell proliferation and transformation, Biochim. Biophys. Acta 1072, S. 129–157

Bossy-Wetzel, E., Bakiri, L. and Yaniv. M. (1997). Induction of apoptosis by the transcription factor c-Jun. EMBO J. 16: 1695–1709.

Boukamp, P.; Breitkreutz, D.; Stark, J.; Fusenig, N. E., (1990). Mesenchyme-mediated and endogenous regulation of growth and differentiation of human skin keratinocytes derived from different body sites. Different. 44:150–161.

Fambrough et al. (1999), Diverse signaling pathways activated by growth factor receptors induce broadly overlapping rather than independent set of genes, Cell 97, S. 727–741

Fusenig, N. E., Epithelial-mesenchymal interactions regulate keratinocyte growth and differentiation in vitro, 1994, I: The Keratinoycte Handbook, I. Leigh, B. lane and F. Watt editors, Cambridge University Press, S. 71–94

Hilberg, F., A. Aguzzi, N. Howels, E. F. Wagner (1993), c-jun is essential for normal mouse development and hepatogenesis, Nature 365, S. 179–181

Iyer et al., (1999), The Transcriptional Program in the Response of Human Fibroblasts to Serum, Science 283, S. 83–87

Lam, Anticancer Drug Des. 12 (1997), 145–167.

Maas-Szabowski, N., Shimotoyodome, A., Fusenig, N. E., (1999) Keratinocyte growth regulation in fibroblast cocultures via double paracrine mechanisms, J. Cell Sci., 112, S. 1843–1853

Rheinwald, J. G. and Green, H.; (1975). Feeder layer system: Serial cultivation of strains of human epidermal keratinocytes. Cell 6:331–344.

Sambrook J, E F Fritsch, T. Maniatis (1989). Molecular Cloning. A Laboratory Manual, 2. Ausgabe. Cold Spring Harbor Laboratory Press, Cold Spring Harbor, N.Y.

Schorpp, M., Jäger, R., Schellander, K., Schenkel, J., Wagner, E. F., Weiher, H. and Angel, P. (1996). The human ubiquitin C promoter directs high ubiquitous expression of transgenes in mice. Nucl. Acids Res 24:1787–1788.

Schorpp-Kistner M., Wang, Z. -Q., Angel, P. and E. F. Wagner (1999). JunB is Essential for the Formation of the mammalian Placenta. EMBO J. 18:934–948.

Schreiber, M. B., B. Baumann, M. Cotten, P. Angel and E. F. Wagner (1995), Fos is an essential component of the mammalian UV response, EMBO J. 14, S. 5338–5349

Schreiber, M., Kolbus, A., Piu, F., Szabowski, A., M öhle-Steinlein, U., Tian, J., Karin, M., Angel, P. and E. F. Wagner (1999). Control of cell cycle progression by c-Jun is p53-dependent. Genes Dev. 13: 607–619.

Smola, H.; Thiekötter, G.; Fusenig, N. E.; (1993). Mutual induction of growth factor gene expression by epidermal-dermal cell interaction. J. Cell Biol. 122: 417–429.

Suh, Anticancer Res. 15 (1995) 233–239.

Stark, H. J., Baur, M., Breitkreutz, D., Mirancea, N., Fusenig, N. E., (1999), Organotypic keratinocyte cocultures in defined medium with regular epidermal morphogenesis and differentiation, J. Invest. Dermatol. 112, S. 681–691

Todaro, G. J. and Green, H. (1963). Quantitative studies of the growth of mouse embryo cells in culture and their development into established lines. J. Cell Biol. 17: 299–313.

Turner, J. Ethnopharmacol. 51 (1–3) (1996), 39–43.

Van Breemen, Anal. Chem. 69 (1997), 2159–2164.

What is claimed is:

1. A genetically modified fibroblast cell comprising:

(a) a gene of the genome of said fibroblast cell encoding a subunit of the transcription factor AP-1, wherein the gene is inactivated and/or
   a modified component of the signal transduction pathway which is acting on the AP-1 transcription factor, resulting in a modified AP-1 activity; and (b) the gene of (a) operably linked to a promoter in an expression vector, wherein the gene encodes the subunit of the transcription factor AP-1 in an inactive form which can, be activated.

2. The genetically modified fibroblast cell according to claim 1, characterized in that the gene from (a) was inactivated by knock-out.

3. The genetically modified fibroblast cell according to claim 1 or 2, characterized in that the gene encoding a subunit of the AP-1 transcription factor is c-jun or junB.

4. The genetically modified fibroblast cell according to claim 1, which is a human fibroblast cell or murine fibroblast cell.

5. The genetically modified fibroblast cell according to claim 4, characterized in that the expression vector contains a sequence coding for a fusion protein from c-Jun and a sequence coding for a tamoxifen binding site (ER).

6. The genetically modified fibroblast cell according to claim 4, characterized in that the expression vector contains a sequence coding for a fusion protein from JunB and a sequence coding for a tamoxifen binding site (ER).

7. The genetically modified fibroblast cell according to claim 1, which was deposited with the DSMZ as DSM ACC2439 on Dec. 21, 1999.

8. The genetically modified fibroblast cell according to any one of claims 1 to 6, which was deposited with the DSMZ under the designation of "cell culture 10JunB-ER™ #7" under DSM ACC2439 on Dec. 21, 1999.

9. A spontaneously established immortal and genetically modified fibroblast cell comprising:
   (a) a gene of the genome of said fibroblast cell encoding a subunit of the transcription factor AP-1, wherein the gene is inactivated and/or
      a modified component of the signal transduction pathway which is acting on the AP-1 transcription factor, resulting in a modified AP-1 activity; and
   (b) the gene of (a) operably linked to a promoter in an expression vector, wherein the gene encodes an active subunit of the transcription factor AP-1 which is expressed only after induction of the promoter and/or the subunit of the transcription factor AP-1 encoded by the gene is present in an inactive form which can be activated.

10. The fibroblast cell according to claim 9 characterized in that the gene from (a) was inactivated by knock-out.

11. The fibroblast cell according to claim 9, characterized in that the gene encoding a subunit of the AP-1 transcription factor is c-jun or junB.

12. The fibroblast cell according to claim 9, which is a human fibroblast cell or murine fibroblast cell.

13. The fibroblast cell according to claim 12, characterized in that the expression vector contains a sequence coding for a fusion protein from c-Jun and a sequence coding for a tamoxifen binding site (ER).

14. The fibroblast cell according to claim 12, characterized in that the expression vector contains a sequence coding for a fusion protein from JunB and a sequence coding for a tamoxifen binding site (ER).

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: A primer

<400> SEQUENCE: 1
atgaggaacc gcattgcg                                                  18

<210> SEQ ID NO 2

-continued

```
<211> LENGTH: 23
<212> TYPE: DNA
<213> ORGANISM: Artificial Sequence
<220> FEATURE:
<223> OTHER INFORMATION: A primer

<400> SEQUENCE: 2
tggagattca agtccccaaa gcc                                           23

<210> SEQ ID NO 3
<211> LENGTH: 40
<212> TYPE: DNA
<213> ORGANISM: Artificial Sequence
<220> FEATURE:
<223> OTHER INFORMATION: A primer

<400> SEQUENCE: 3
acggctgcca gttcggctag gggtcaaggg acacgccttc                         40

<210> SEQ ID NO 4
<211> LENGTH: 40
<212> TYPE: DNA
<213> ORGANISM: Artificial Sequence
<220> FEATURE:
<223> OTHER INFORMATION: A primer

<400> SEQUENCE: 4
gtctggactc gaggatcccc gaaggcgtgt cccttgaccc                         40

<210> SEQ ID NO 5
<211> LENGTH: 24
<212> TYPE: DNA
<213> ORGANISM: Artificial Sequence
<220> FEATURE:
<223> OTHER INFORMATION: A primer

<400> SEQUENCE: 5
cagaccgtac cggaggcacg cagc                                          24

<210> SEQ ID NO 6
<211> LENGTH: 23
<212> TYPE: DNA
<213> ORGANISM: Artificial Sequence
<220> FEATURE:
<223> OTHER INFORMATION: A primer

<400> SEQUENCE: 6
tggagattca agtccccaaa gcc                                           23
```